(12) United States Patent
Nelson et al.

(10) Patent No.: US 8,257,519 B1
(45) Date of Patent: *Sep. 4, 2012

(54) HOST-GUEST COMPLEXES OF LIQUID ENERGETIC MATERIALS AND METAL-ORGANIC FRAMEWORKS

(75) Inventors: Andrew P. Nelson, Ridgecrest, CA (US); Nirupam J. Trivedi, Ridgecrest, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/835,572

(22) Filed: Jul. 13, 2010

(51) Int. Cl.
*C06B 47/00* (2006.01)
*C06B 45/00* (2006.01)
*C06B 25/00* (2006.01)
*D03D 23/00* (2006.01)
*D03D 43/00* (2006.01)

(52) U.S. Cl. ............... 149/1; 149/2; 149/88; 149/109.2; 149/109.4

(58) Field of Classification Search ............ 149/1, 2, 149/88, 109.2, 109.4
See application file for complete search history.

(56) References Cited

U.S. PATENT DOCUMENTS 6,833,037 B1 * 12/2004 Hallam et al. ............ 149/19.91
2008/0245252 A1 * 10/2008 Erickson et al. ............ 102/204

OTHER PUBLICATIONS

Odbadrakh et al., Abstract submitted to the American Physical Society Mar. 2009.*
Odbadrakh et al. "Smart Nanoporous Preconcentrator of Explosives Based on MOF-5" Abstract Mar. 2009 meeting of the American Physical Society.*

* cited by examiner

*Primary Examiner* — James McDonough
(74) *Attorney, Agent, or Firm* — Charlene A. Haley

(57) ABSTRACT

A process for making metal-organic frameworks and metal-organic frameworks having host-guest complexes of either liquid energetics, solid energetics, or solid oxidizers.

10 Claims, 19 Drawing Sheets

HOST-GUEST COMPLEXES OF LIQUID ENERGETIC MATERIALS AND METAL-ORGANIC FRAMEWORKS

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to metal-organic frameworks, and more specifically, metal-organic frameworks having host-guest complexes of either liquid energetic, solid energetic, or solid oxidizers.

Figure 1:
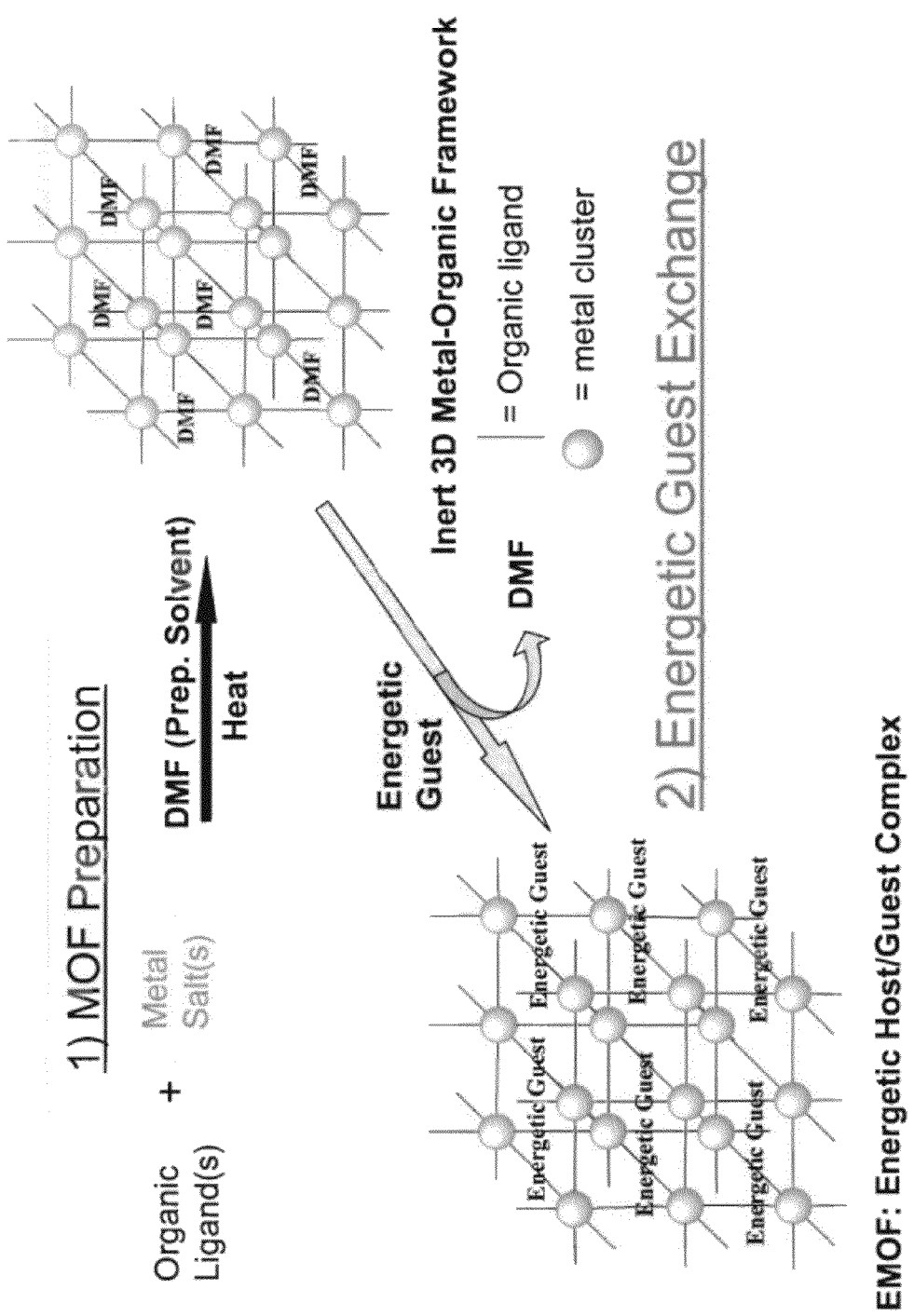
FIG. 1 is a flow chart illustrating host-guest complexes of liquid energetic materials and metal-organic frameworks, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE EMBODIMENTS OF THE INVENTION

Embodiments of the invention generally relate to metal-organic frameworks, and more specifically, metal-organic frameworks having host-guest complexes of either liquid energetics, solid energetics, or solid oxidizers.

For many years the navy has been actively researching new advances in high performance insensitive munitions (IM). This technology represents a new IM approach whereby the thermal stability of energetic materials can be enhanced by creating host-guest complex with a three dimensional porous framework.

The attraction/interaction of the host can be any chemical or physical attraction/interaction including, but not limited to, dipole-dipole, covalent, ionic, hydrogen bonding, electrostatic, Vander walls etc. The use of any guest that is liquid at room temperature, can melt at a temperature significantly below its decomposition temperature or can be dissolved in a suitable carrier media could be incorporated in a MOF using this procedure.

The following examples are for illustration purposes only and not to be used to limit any of the embodiments.

An aspect of the invention generally relates to a host-guest complex as an energetic component in an insensitive munitions weapons system including, an effective amount of at least one host having organic ligand(s) combined with an effective amount of at least one metal salt to form ligand(s)/metal salt(s) complex, where the ligand(s)/salt(s) complex form at least one porous framework host configured to house a guest, and at least one guest being a liquid energetic material/explosive, where the guest is housed substantially within the host.

A further aspect of the invention includes a host-guest insensitive munitions complex framework having an effective amount of at least one host having organic ligand(s) combined with an effective amount of at least one metal salt to form ligand(s)/metal salt(s) complex, where the ligand(s)/metal salt(s) complex form at least one porous framework host configured to house a guest, and at least one guest being a liquid energetic material/explosive, where the guest is housed substantially within the host.

Another aspect of the invention generally relates to a process for making a host-guest complex as an energetic component of insensitive munitions weapons system including, combining an effective amount of at least one host having organic ligand(s) with an effective amount of at least one metal salt, forming ligand(s)/metal salt(s) complex, forming at least one porous framework host configured to house a guest from the ligand(s)/salt(s) complex, and providing at least one guest being a liquid energetic material/explosive, and incorporating the guest such that the guest being housed substantially within the host.

Embodiments of the invention include host(s) where the organic ligand(s) and the metal salt(s) form ligand/metal cluster(s) complex(es). In embodiments, the organic ligand(s) and the metal salts(s) form the $Zn_2NDC_2DPNI$ and Basolite A100 host MOFs. The system may be in the form of an array of three dimensional porous framework(s). Embodiments of the system may further include a solvothermal combination mechanism. In embodiments, the solvothermal combination mechanism includes at least one of dimethylformamide (DMF) solvent and a pre-determined amount of temperature applied to the complex depending on the ligand(s)/metal salt(s) complex utilized.

The ligand(s) include, but are not limited to, at least one of 2-6 naphthalenedicarboxylic acid (NDC), N,N'-di(4pyridyl)-1,4,5,8-naphthalenetetracarboxydiimide (DPNI), 1,4 benzene dicarboxylic acid (BDC), and any combination thereof. Embodiment of the invention includes, but is not limited to, liquid (or even liquid high explosive) energetic/explosive(s) having at least one of n-butyl-2-nitratoethylnitramine (BuNENA), butanetriol trinitrate (BTTN), tetramethylolethane trinitrate (TMETN), triethylenegylcol dinitrate (TEGDN), nitroglycerine (NG), diethyleneglycol dinitrate (DEGDN), and other similar material, and any combination thereof. The system may further include replacement of solvent with the liquid high explosive.

The system may also include a porous framework(s) in the form of an amorphous powder(s), crystalline powder(s), and single crystal(s). In embodiments, the porous framework(s) is formed by at least one group of mechanisms involving change in temperature(s), pressure, solvent(s), gas(es), volatile curing agent(s), and any combination thereof.

Host-Guest Complexes of Liquid Energetic Materials and Metal-Organic Frameworks

Metal-Organic Frameworks (MOFs) represent an emerging class of materials characterized by permanent microporosity, extremely high surface areas and high thermal stability. MOFs have received much attention recently for their ability to trap small organic molecules for applications including chemical energy storage, physical separation and catalysis. This research takes advantage of the MOFs tunable microporosity and high thermal stability and utilizes MOFs as hosts for small molecule energetic materials. It is demonstrated that energetic materials can be trapped inside a MOF host and once occluded this host-guest relationship leads to an increase in the thermal stability of the energetic guest.

In order to satisfy the Navy's In house Laboratory Independent Research (ILIR) program requirements, the information regarding the preparation and characterization of these energetic host guest complexes was recently reported on 16 Aug. 2009 in an oral presentation at the 238th American Chemical Society National Meeting in Washington D.C.

Insensitive munitions (IM) compliant weapons systems are now mandated by both US law and Department of Defense (DoD) policy. In order to construct a full IM compliant weapons system, it is logical to attempt the system construct from individual, IM compliant components. In most weapons systems, those components which cause the system to fail in response to IM stimuli are the energetic materials responsible for the weapons performance. To this end it is necessary to develop energetic materials that have high explosive performance with decreases sensitivity.

Many of the threats posed to a weapon system and therefore tested for in IM tests involve the unexpected thermal initiation of the weapons energetic components by either fuel fire, slow heating, hot fragment, and hot bullet. Increasing the thermal stability of the energetic ingredients is identified as one objective toward improving the explosives response to thermal stimuli.

Metal-Organic Frameworks (MOFs) are an emerging class of new materials in which an inestimable number of small organic ligands can be combined with a variety of metal salts to create a nearly infinite array of three dimensional porous frameworks. MOFs are characteristically highly crystalline materials with high accessible surface areas. They are in most cases also extremely thermally stable. It is common for MOFs no to thermally decompose until temperatures above 400 degrees centigrade. This research postulated the encapsulation of a thermally sensitive energetic material (explosive) inside the accessible pores of a highly thermally stable porous material as a method for increasing the thermal stability of the energetic material.

While the adsorption and encapsulation of small organic molecules in MOFs has been extensively studied by the authors and others, this represents the first preparation and characterization of a MOF host guest complex in which the guest is a liquid high explosive.

In Summary the embodiments of the invention addresses these problems. Novel host guest complexes in which an energetic small molecules is successfully trapped in the accessible pores of an inert MOFs. The encapsulation of energetic materials reduces the sensitivity of the energetic guest by imparting some of the thermal stability of the host onto the energetic guest.

The MOF host $(Zn_2(NDC)_2DPNI)$ utilized in this study is prepared by the solvothermal combination of zinc nitrate hexahydrate $(Zn(NO_3)_2 6H_2O$, 2-6 naphthalenedicarboxylic acid (NDC), and N,N'-di(4pyridyl)-1,4,5,8-naphthalenetetracarboxydiimide (DPNI) in dimethylformamide (DMF) as described by MA. et. al. Inorg. Chem. 2005, 44, 4912-4914. The MOF host is therefore prepared with DMF occupying the pores and is isolated as large yellow rectangular crystals, designated $Zn_2(NDC)_2DPNI$-DMF shown in FIG. 1.

In order to definitively show the incorporation of the desired liquid energetic, within the pores of the MOF single crystal x-ray analysis of the energetically doped MOF crystals is desirable. To accomplish the single crystal to single crystal exchange of DMF for a liquid energetic material in the MOF host, attention must be taken to leave the MOF crystals as undisturbed as possible. Furthermore, the crystals must remain wet throughout the guest exchange procedure. In this study, the single crystal to single crystal exchange of DMF with butanetriol trinitrate (BTTN) was demonstrated. Bulk samples of the host MOF exchanged with tetramethylolethane trinitrate (TMETN), triethyleneglycol dinitrate (TEGDN), and n-butyl-2-nitratoethylnitramine (BuNENA) have been prepared and characterized by analogy to the $Zn_2$(NDC)$_2$DPNI-BTTN complex.

Single Crystal to Single Crystal Exchange of DMF for BTTN in $Zn_2$(NDC)$_2$DPNI.

Once the $Zn_2$(NDC)$_2$DPNI-DMF crystals have been prepared, the BTTN is introduced by layering an equal volume of liquid energetic on top of the preparative solution of MOF crystals in DMF. The DMF is partially removed from the bottom of the reaction vial and the volume of removed DMF is replaced with neat BTTN. This procedure is completed three times initially to heavily dilute, with BTTN, the DMF surrounding the MOF crystals. Following the initial additions of BTTN, the samples are allowed to stand undisturbed for 15 days at which point the lower half of the reaction medium is removed and replaced with fresh BTTN. This procedure is repeated three times prior to the MOF crystals being analyzed by x-ray diffraction.

Figure 13:
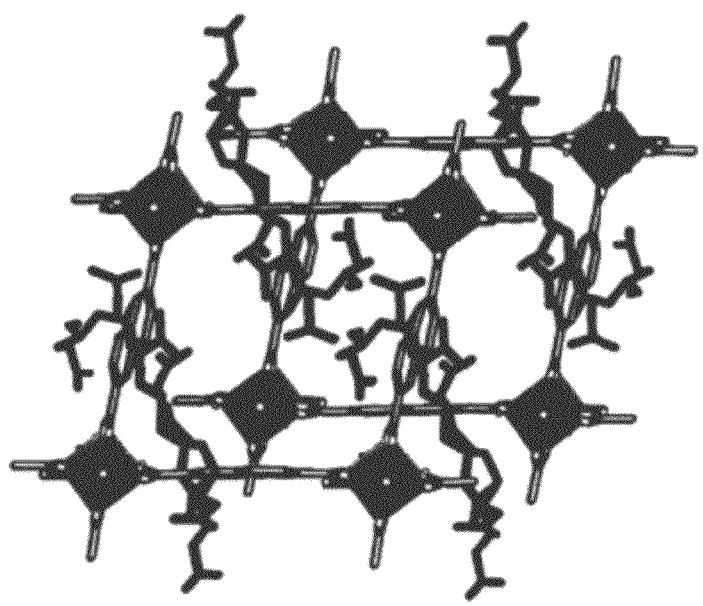
FIGS. 13a and 13b are side perspective views of a crystal structure of $Zn_2NDC_2DPNI$-nBTTN. (a) View from the axis defined by the DPNI ligands showing the 2-fold interpenetrated net with BTTN molecules shown in black (Zn=dark gray polyhedron, C=gray, N=white, O=light gray). (b) space filling diagram showing BTTN (shown in black) occupying the largest pores of the MOF.
Figure 13B:
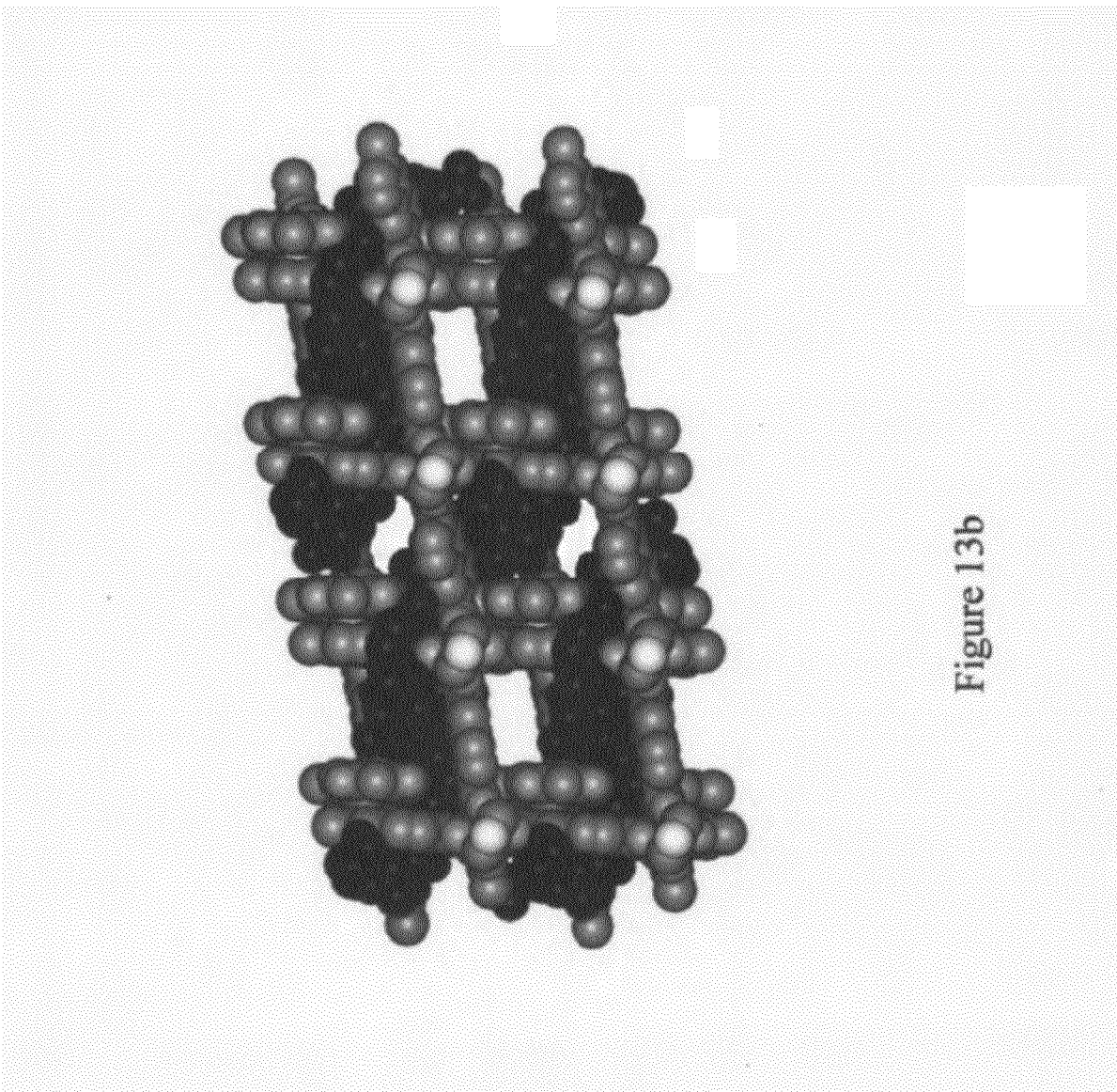

FIGS. 13a and 13b are chemical structures that are crystal structures of $Zn_2NDC_2$DPNI-nBTTN. (a) View from the axis defined by the DPNI ligands showing the 2-fold interpenetrated net with BTTN molecules shown in black (Zn dark gray polyhedron, C=gray, N=white, O=light gray). (b) space filling diagram showing BTTN (shown in black) occupying the largest pores of the MOF.

X-Ray Analysis of $Zn_2NDC_2$DPNI-BTTN:

A thin yellow plate of dimensions 0.23×0.14×0.06 mm$^2$ was mounted on a MiteGen MicroMesh using a small amount of Cargille Immersion Oil. Data was collected on a Bruker three circle platform diffractometer equipped with a SMART APEX II CCD detector. The crystals were irradiated using graphite monochromated MoK$_{alpha}$ radiation (lambda=0.71073). An MSC X-stream low-temperature device was used to keep the crystals at a constant 123(2) deg. K during collection. The structure was solved and refined with the aid of the programs in the SHELXTL-plus [v6.12] system of programs. The full-matrix least-squares refinement on $F^2$ included atomic coordinates and anisotropic thermal parameters for all non-H atoms involved in the framework. Only the BTTN molecule with was fully occupied was refined with anisotropic thermal parameters, the three partially occupied BTTN molecules ranged in populations from 0.73-0.39. The H atoms of the framework were included using a riding model. The crystal was a twin and refined to a ratio of 70:30 for the two twin components. (shown above)

Bulk Preparation of $Zn_2NDC_2$DPNI-BTTN, $Zn_2NDC_2$DPNI-TMETN, $Zn_2NDC_2$DPNI-TEGDN, and $Zn_2NDC_2$DPNI-BuNENA.

Crystals of $Zn_2NDC_2$DPNI-DMF were isolated by filtration from the preparative DMF solution and washed with DMF to remove any residual reagent material. Once isolated, the neat energetic liquids were added directly to the MOF crystals and allowed to stand. for 7 days. Every seven days the energetic soaking solution is replaced with fresh nitrate ester and this procedure is repeated three times. The nitrate ester/MOF host guest complexes are then isolated by filtration and allowed to dry.

Differential scanning calorimetry (DSC) and thermal gravimetric analysis (TGA) of $Zn_2NDC_2$DPNI-BTTN, $Zn_2NDC_2$DPNI-TMETN, $Zn_2NDC_2$DPNI-TEGDN, and $Zn_2NDC_2$DPNI-BuNENA.

Figure 2:
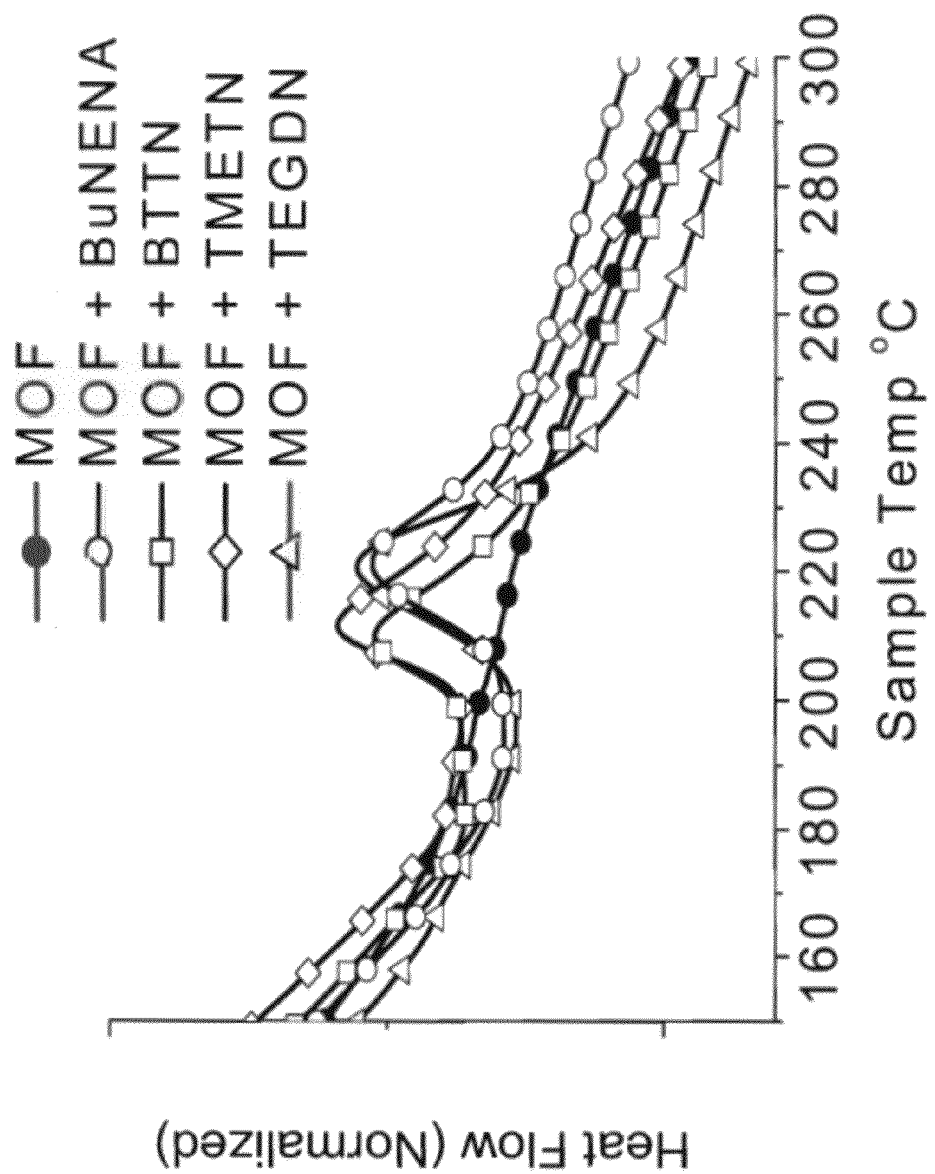
FIG. 2 is a graph illustrating differential scanning calorimetry (DSC) traces of $Zn_2(NDC)_2(DPNI)$ complexes with dimethylformamide (DMF), n-butyl-2-nitratoethylnitramine (BuNENA), butanetriol trinitrate (BTTN), tetramethylolethane trinitrate (TMETN) and triethyleneglycol dinitrate (TEGDN), according to embodiments of the invention.

The bulk nitrate ester/MOF host guest complexes were characterized by DSC and TGA to show inclusion of the energetic material within the pores of the framework as well as the thermal effect imparted to the energetic material as a consequence of MOF encapsulation. The DSC traces of the energetic MOF complexes clearly show the exothermic decomposition of energetic nitrate esters at peak temperatures ranging from 210° C. to 222° C. (FIG. 2). By comparison to the literature values for the decompositions of the neat, non-encapsulated nitrate esters, an average increase in peak decomposition temperature of 17.65° C. as a result of encapsulation within the MOF pores was observed. Table 1 shows the effect of encapsulation on the thermal decomposition of BTTN, TMETN, TEGDN and BuNENA.

TABLE 1

Decomposition temperatures of energetic nitrate esters and MOF encapsulated nitrate esters.

| | Onset Point (° C.) | Peak (° C.) |
|---|---|---|
| BuNENA | 171.4 | 198.2 |
| MOF(BuNENA) | 204.3 | 220.2 |
| BTTN | 178.5 | 197.3 |
| MOF(BTTN) | 194.8 | 210.7 |
| TMETN | 182.1 | 195.5 |
| MOF(TMETN) | 198.8 | 211.5 |
| TEGDN | 179.4 | 202.9 |
| MOF(TEGDN) | 199.4 | 222.1 |

Figure 3:
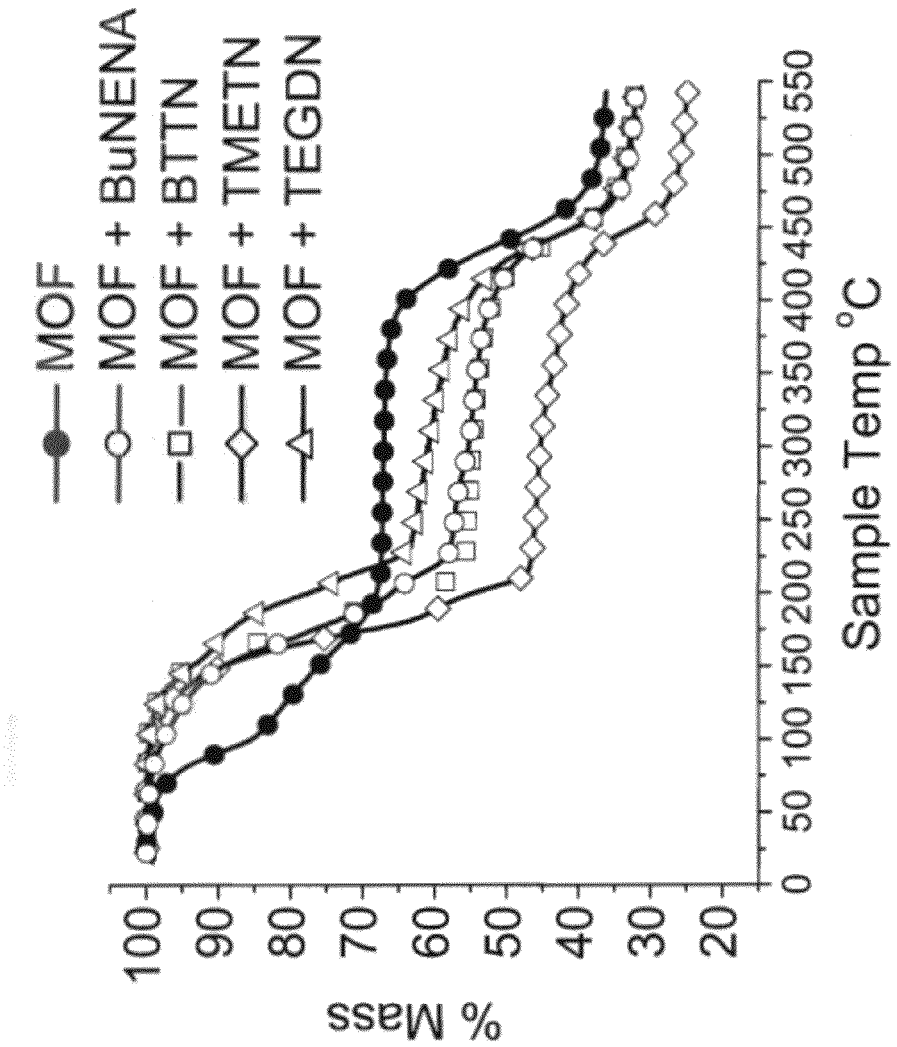
FIG. 3 is a graph illustrating thermal gravimetric analysis (TGA) traces of $Zn_2(NDC)_2(DPNI)$ complexes with dimethylformamide (DMF), n-butyl-2-nitratoethylnitramine (BuNENA), butanetriol trinitrate (BTTN), tetramethylolethane trinitrate (TMETN) and triethyleneglycol dinitrate (TEGDN), according to embodiments of the invention.

TGA traces of the nitrate ester MOF complexes (FIG. 3) show large shifts in the thermal decomposition of the encapsulated guest by comparison to the starting $Zn_2NDC_2$DPNI-DMF complex. On average, around 44% by weight of nitrate ester is adsorbed by the MOF further indicating that the internal MOF pore volume is occupied by the new guest. The identity of the new energetic guest has been verified with coupled TGA and fourier transform infrared (FTIR) spectroscopy (TGA-IR) by comparing the IR spectrum of the liberated energetic guest to the IR spectra of the neat nitrate ester. The TGA-IR traces as well as the single crystal x-ray analysis indicate that the exchange of the preparative DMF solvent for the new energetic guest is quantitative.

Host-Guest Complexes of Solid Energetic Materials and Metal-Organic Frameworks

An aspect of the invention includes host-guest complex as an energetic component in an insensitive munitions weapons system, having an effective amount of at least one host having organic ligand(s) combined with an effective amount of at least one metal salt(s) to form ligand(s)/metal cluster(s) complex, where the ligand(s)/metal cluster(s) complex form at least one porous framework host configured to house a guest, and at least one guest being a solid energetic material and/or high solid energetic material, where guest is housed substantially within the host.

Another aspect of the invention includes a process for making a host-guest complex as an energetic component in insensitive munitions weapons, including combining an effective amount of at least one host having organic ligand(s) with an effective amount of at least one metal salt, forming ligand(s)/metal cluster(s) complex, forming at least one porous framework host configured to house a guest from the ligand(s)/metal cluster(s) complex, and providing at least one guest being a solid energetic material, and incorporating the guest such that the guest being housed substantially within the host.

Yet another aspect of the invention includes a host-guest complex as an energetic component in an insensitive munitions complex framework having an effective amount of at least one host having organic ligand(s) combined with an effective amount of at least one metal salt to form ligand(s)/metal cluster(s) complex, where the ligand(s)/metal cluster(s) complex form at least one porous framework host configured to house a guest, and at least one guest being a solid energetic material, where the guest is housed substantially within the host.

Embodiments of the invention include a host where the organic ligand(s) and the metal salts(s) form ligand/metal cluster(s) complex(es). In embodiments, the organic ligand(s) and the metal salts(s) form the $Zn_2NDC_2DPNI$ and Basolite A100 host MOF. The system may be in the form of an array of three dimensional porous framework(s). Embodiments of the system may further include a solvothermal combination mechanism. In embodiments, the solvothermal combination mechanism includes at least one of dimethylformamide (DMF) solvent and a pre-determined amount of temperature applied to the complex depending on the ligand(s)/metal salt(s) complex utilized.

The ligand(s) include, but are not limited to, at least one of 2-6 naphthalenedicarboxylic acid (NDC), N,N'-di(4pyridyl)-1,4,5,8-naphthalenetetracarboxydiimide (DPNI), 1,4-Benzene dicarboxylic acid (BDC) and any combination thereof.

The system may also include a porous framework(s) in the form of an amorphous powder(s), crystalline powder(s), and single crystal(s). In embodiments, the porous framework(s) is formed by at least one group of mechanisms involving change in temperature(s), pressure, solvent(s), gas(es), volatile curing agent(s), and any combination thereof.

The system may further include the removal of the solvent before the addition of the solid energetic material. Embodiments of the invention have solid energetic materials including, but are not limited to, at least one of trinitrotoluene, dinitrotoluene, nitrotoluene, trinitrobenzene, dinitrobenzene and any combination thereof. Embodiments of the invention include a guest having at least one high explosive. In embodiments, the ligand(s)/metal cluster(s) complex further includes the step of activating the complex by heat and reduced pressure before subjecting the activated complex to the guest. In embodiments, the activated complex and guest combination further includes the step of heating the combination into a molten guest, solid host mixture.

The MOF host designated Basolite™ A100 utilized in this study is commercially available from Sigma-Aldrich and must be activated prior to energetic guest incorporation. As per the manufacturers' specifications, the Basolite™ A100 is the MOF host and is activated by heating the material to 250° C. under reduced pressure for a period of 24 hrs. The activated MOF is then subjected immediately to the energetic guest inclusion procedure or stored in a desiccator. Trinitrotoluene (TNT) was chosen as the solid energetic material for this study, however; any energetic material of appropriate dimension, which melts at a temperature significantly below its decomposition temperature could be incorporated in a MOF using this procedure.

Bulk Preparation of Basolite™ A100-TNT Complex

To the thy powder of activated Basolite™ A100 was added to solid crystals of TNT. The dry mixture was then placed into an oven and heated slowly to 90° C. The oven temperature was maintained for 72 hrs. After 72 hrs the molten TNT/MOF mixture was filtered hot and collected for evaluation. It is clear from the material collected following the hot filtration that some residual TNT remains on the surface of the MOF particles. Washing this material with acetone at room, temperature will remove any residual TNT from the surface of the MOF particles. The Basolite™ A100-TNT complexes both with and without residual TNT on the particle surfaces were characterized by differential scanning calorimetry (DSC), thermal gravimetric analysis (TGA) and solid probe mass spectrometry (SPMS).

Figure 4:
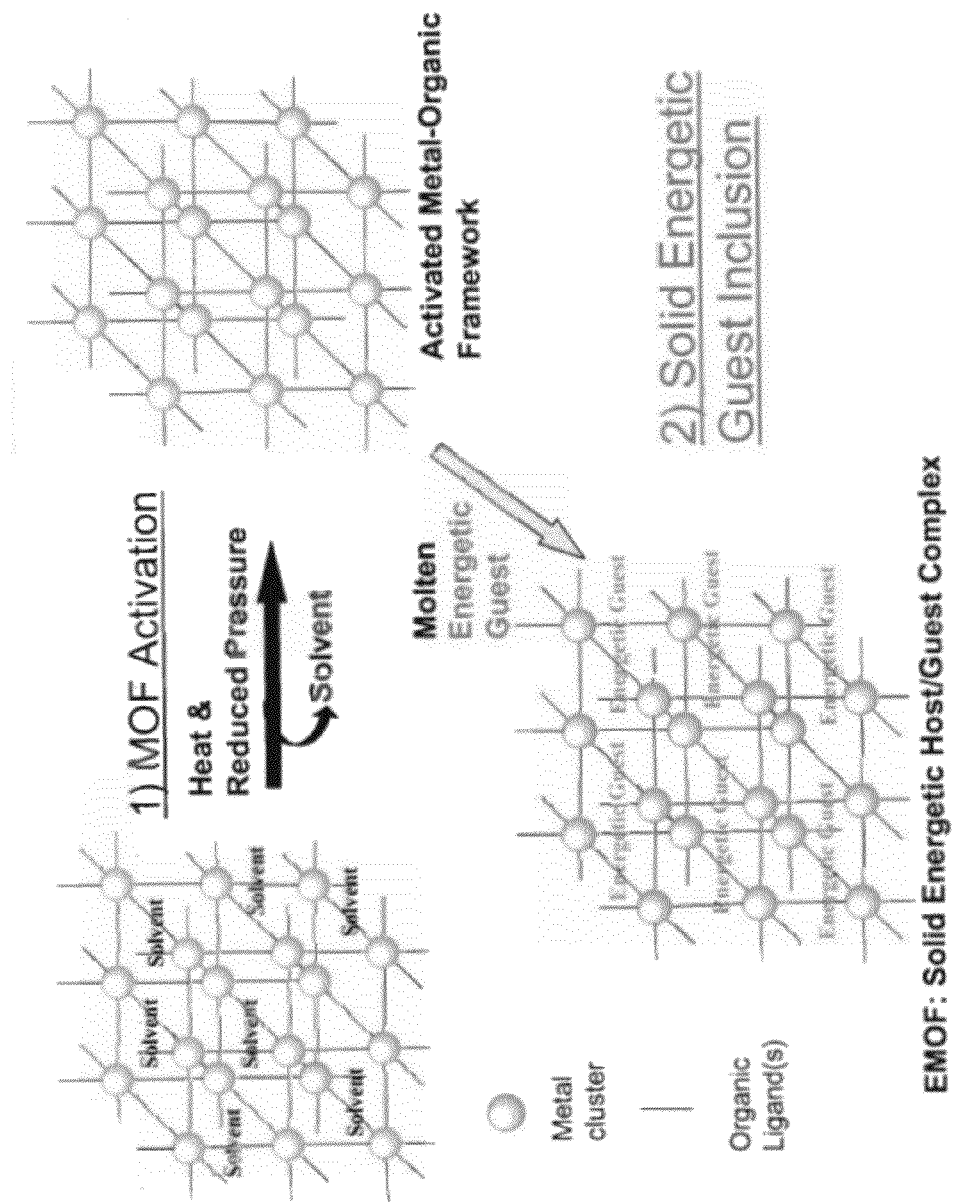
FIG. 4 is a flow chart illustrating host-guest complexes of solid energetic materials and metal-organic frameworks, according to embodiments of the invention.

DSC and SPMS of the Basolite™ A100-TNT Host/Guest Complex as Shown in FIG. 4.

Figure 5:
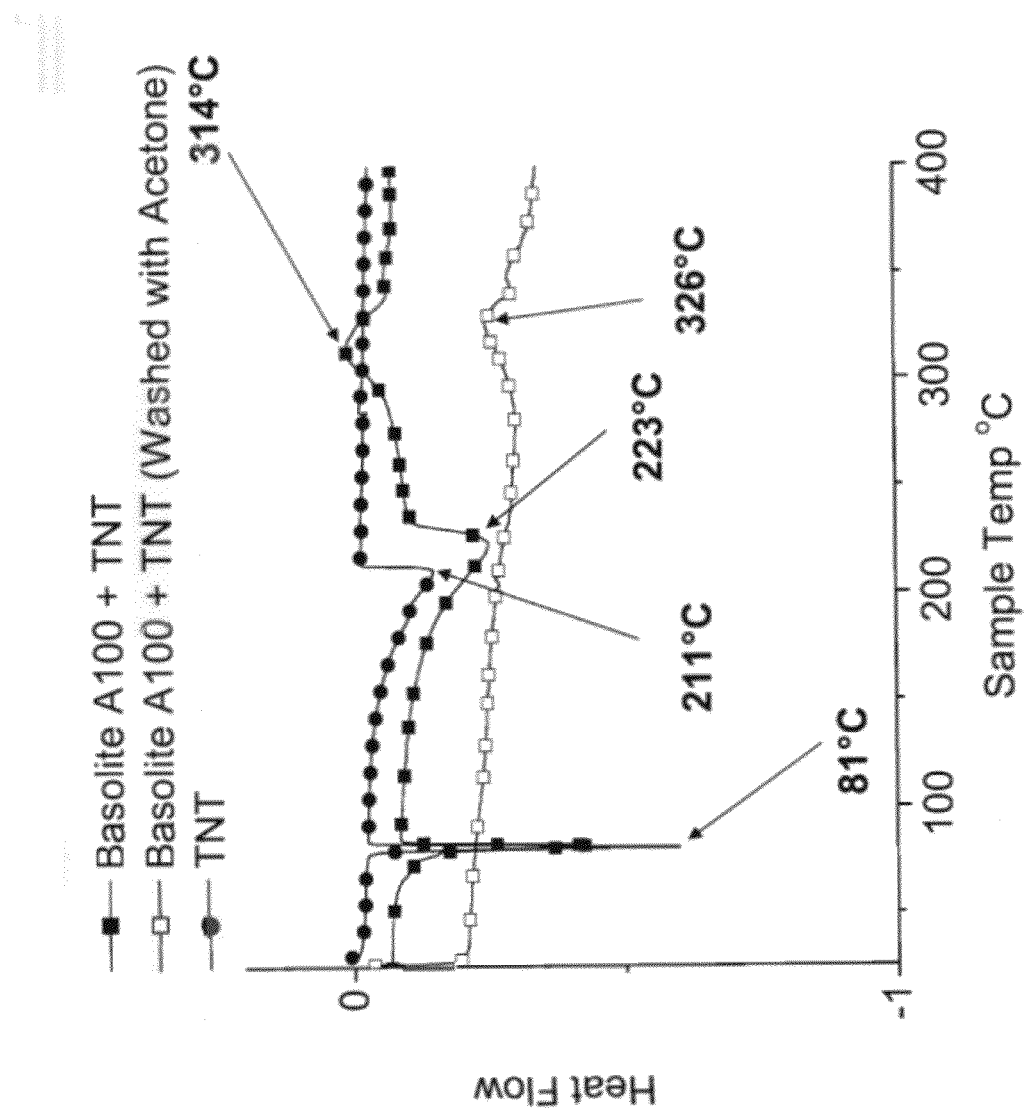
FIG. 5 is a graph illustrating DSC traces of Basolite™ A100 complexes with trinitrotoluene (TNT), according to embodiments of the invention.

The DSC traces of the energetic MOF complexes clearly show the exothermic decomposition of the TNT over 300° C. (FIG. 5). While the neat TNT control sample shows two distinct thermal events. The first is endothermic melting of TNT at 81° C. followed by endothermic decomposition, typical of a melt phase decomposition reaction, with a peak at 211° C. The MOF-TNT complex in which the surface coating TNT remains, shows three distinct thermal events. An endothermic melting of TNT at 81° C. and an endothermic decomposition with a peak at 226° C., and an exothermic decomposition with a peak at 314° C. The endothermic peaks at 81 and 226 are similar to the melting and subsequent decomposition of the TNT control sample. This endothermic decomposition can therefore be assigned to the TNT bound to the surface of the MOF particles and the exothermic decomposition with a peak at 314° C. can therefor be assigned as the decomposition of the solid energetic occluded within the MOF pores, In contrast the MOF-TNT complex from which the surface bound TNT has been washed away shows only a single thermal event, an exothermic decomposition with a peak at 326° C. This DSC trace clearly indicates that only the TNT occluded within the pores is present in the complex.

Figure 6:
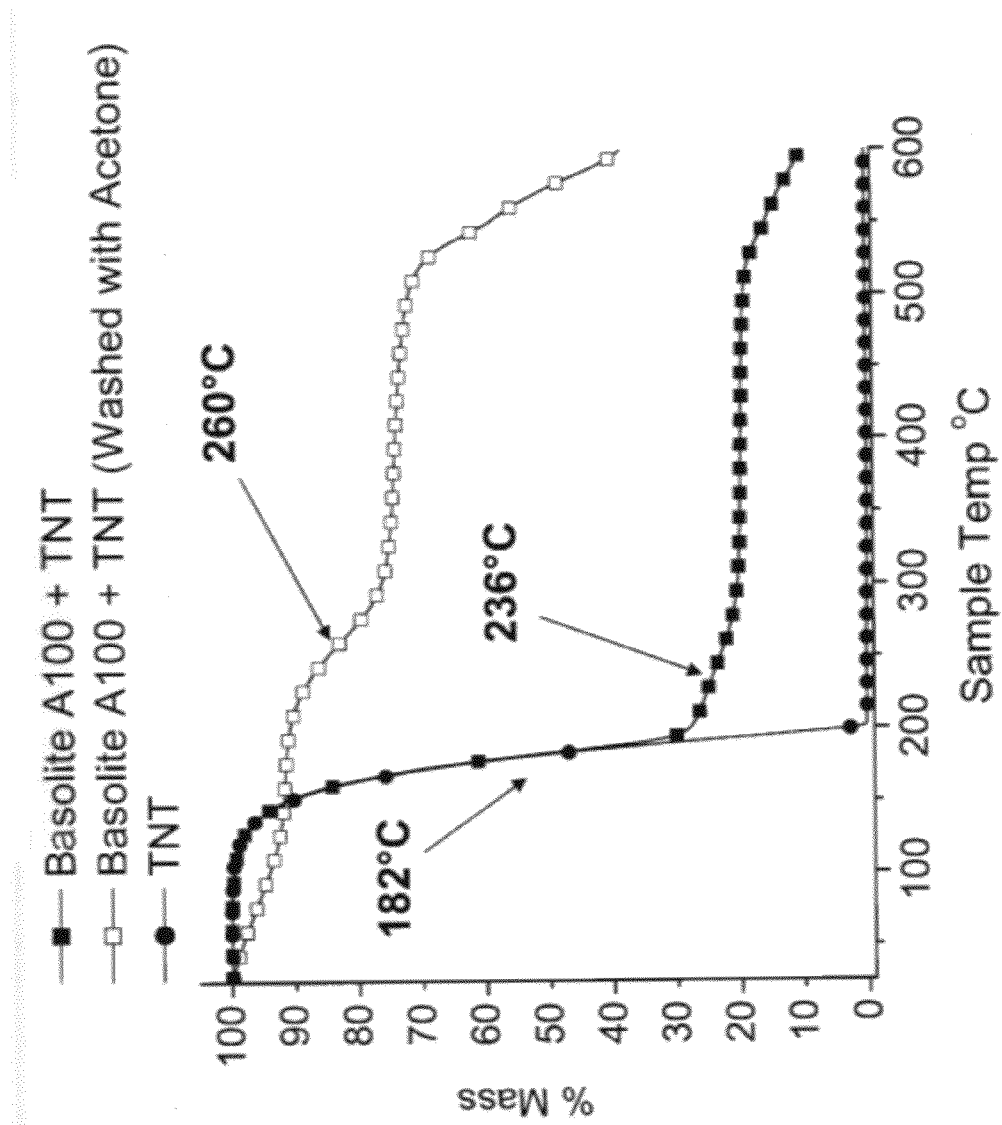
FIG. 6 is a graph illustrating TGA traces of Basolite™ A100 complexes with TNT, according to embodiments of the invention.

The TGA traces mirror the results of the DSC experiments (FIG. 6). For the control TNT and the MOF-TNT complex with surface bound energetic, we see a large mass loss with a half height temperature around 182° C. In addition to the first drop in the TGA curve, the MOF-TNT complex shows a second mass loss curve at a half height temperature of 236° C. By comparison the MOF-TNT complex from which the surface TNT has been washed shows no mass loss corresponding to neat or surface bound TNT but rather a mass drop with a half height temperature of 260° C. corresponding to the loss of TNT from within the MOF pores.

Figure 7A:
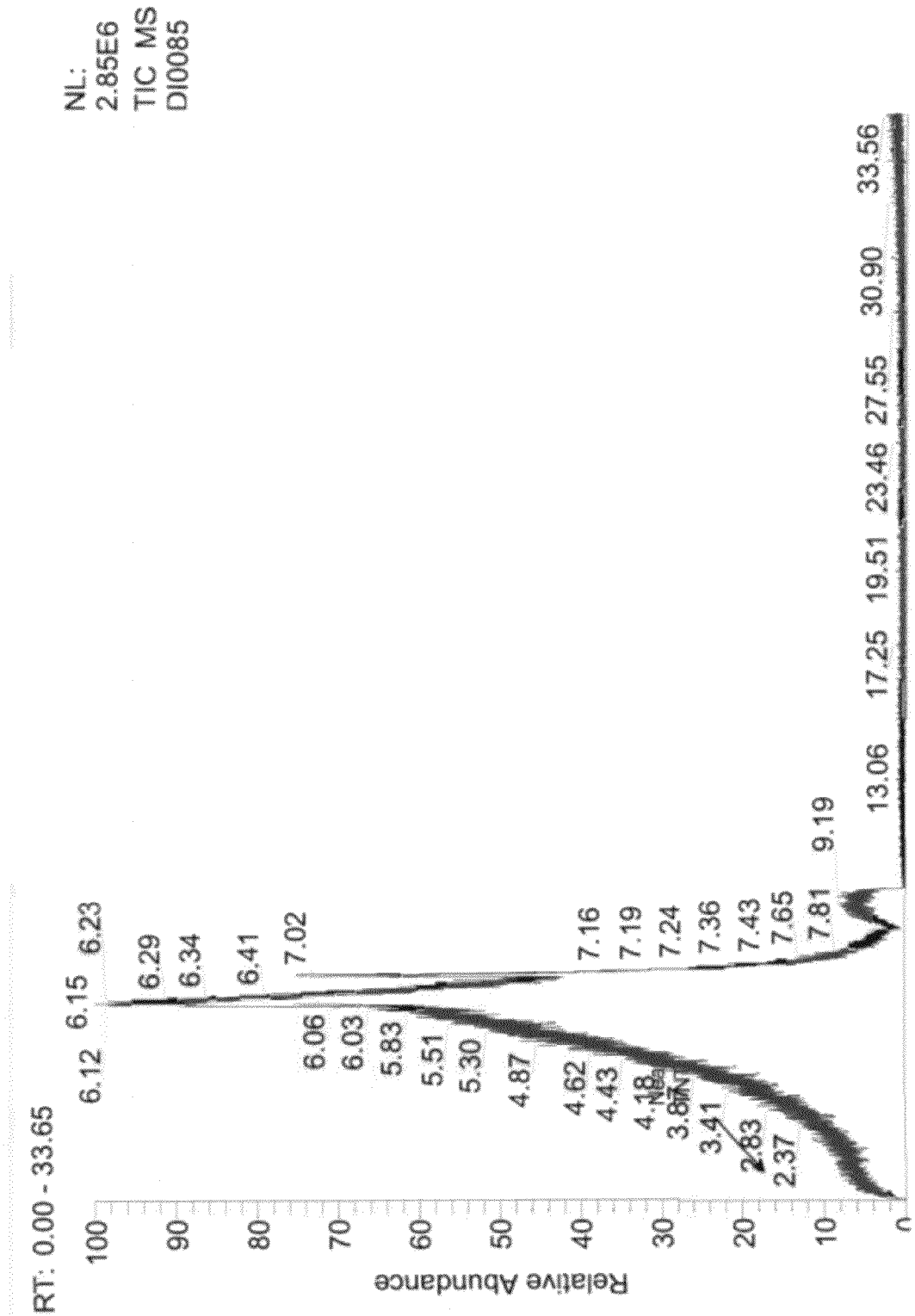
FIG. 7A is a graph illustrating solid probe mass spectrometry (SPMS) Data from TNT measuring the Total Ion Chromatogram for Neat TNT versus time and temperature, according to embodiments of the invention.
Figure 7B:
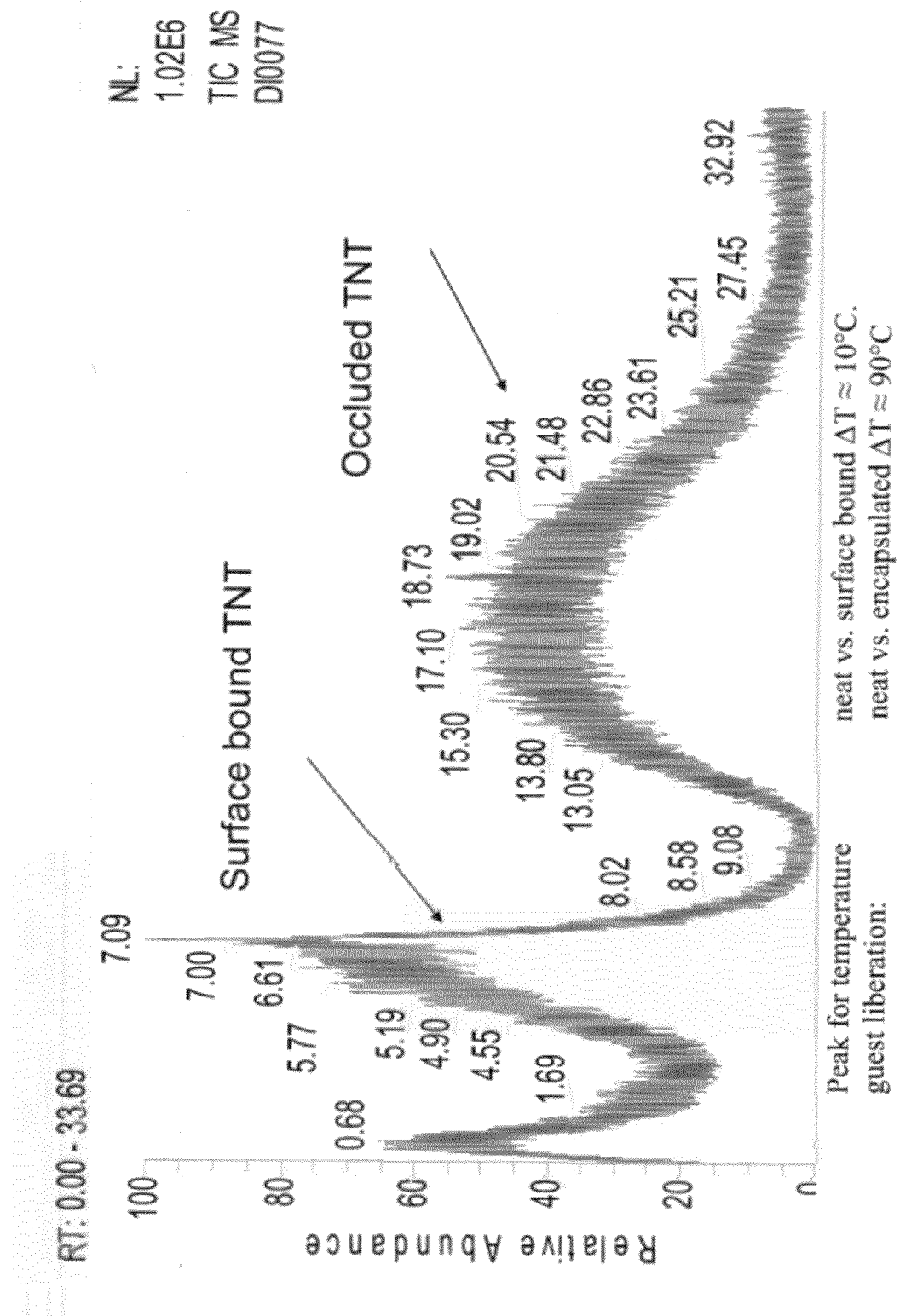
FIG. 7B is a graph illustrating SPMS Data from Basolite™ A100-TNT complex measuring the Total Ion Chromatogram of TNT versus time and temperature, according to embodiments of the invention. (right)

In the solid probe mass spectrometry (SPMS) tests, the samples are heated at the same rate used for the DSC and TGA experiments but at a reduced pressure necessary for the coupling to the mass spectrometer (FIGS. 7A and 7B). In this experiment, the decomposition products are therefore identified by there characteristic m/z signal. The first conclusion drawn form the SPMS experiments is that the decomposition products from the control TNT sample match those measured for the MOF-TNT complexes. This confirms the quantitative inclusion of TNT in the MOF pores. Secondly, the SPMS data mirror the results from the DSC and TGA experiments in which the decomposition products of the neat TNT and the surface bound TNT are produced at a much lower temperature that those observed for the TNT occluded within the MOF pores.

In these tests it was observed that the consequence of encapsulating the energetic guest within the pores of the MOF framework, was a 100° C. increase in the guest's thermal decomposition temperature. These tests confirm the hypothesis that encapsulation of a solid. energetic material within the pores of a thermally stable host brings about significant enhancement in the thermal stability of the energetic guest.

Figure 8:
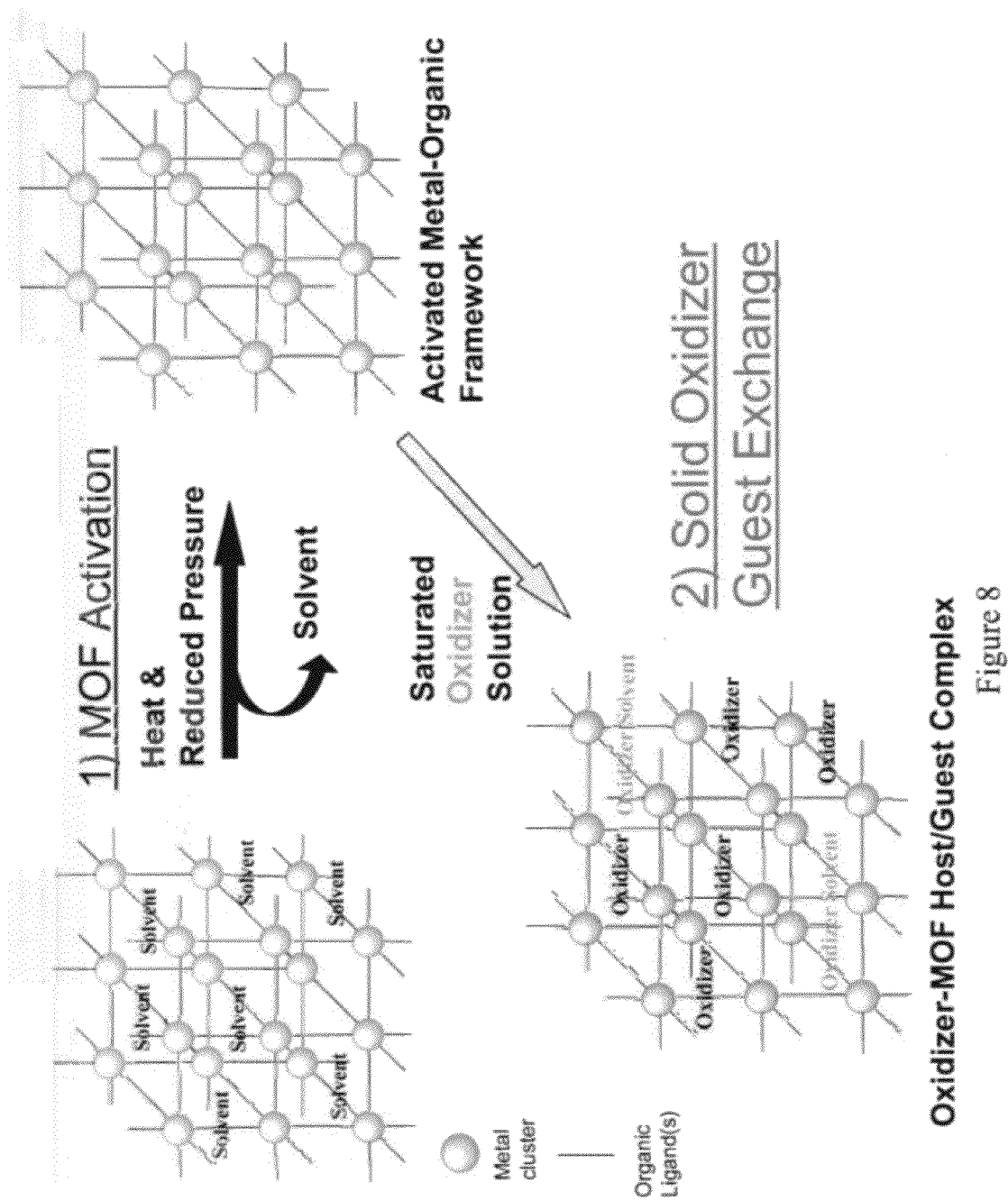
FIG. 8 is a flow chart illustrating host-guest complexes of solid oxidizers and metal-organic frameworks, according to embodiments of the invention.

Host-Guest Complexes of Solid Oxidizers and Metal-Organic Frameworks Shown in FIG. 8.

An aspect of the invention relates to a host-guest complex as an energetic component in an insensitive munitions weapons system, including an effective amount of at least one host having organic ligand(s) combined with an effective amount of at least one metal salts(s) to form ligand(s)/metal cluster(s) complex, where the ligand(s)/metal cluster(s) complex form at least one porous framework host configured to house a guest, and at least one guest being an oxidizer, where the guest is housed substantially within the host. In embodiments, the oxidizer can be a solid oxidizer.

Another aspect of the invention relates to a process for making a host-guest complex as an energetic component in insensitive munitions weapons, including combining an effective amount of at least one host having organic ligand(s) with an effective amount of at least one metal salt, forming a ligand(s)/metal cluster(s) complex, forming at least one porous framework host configured to house a guest from the ligand(s)/metal cluster(s) complex, and providing at least one guest being an oxidizer, and incorporating the guest such that the guest being housed substantially within the host.

Yet another aspect of the invention relates to a host-guest complex as an energetic component in an insensitive munitions complex framework, including an effective amount of at least one host having organic ligand(s) combined with an effective amount of at least one metal salt to form ligand(s)/metal cluster(s) complex, where the ligand(s)/metal cluster(s) complex being combined to form at least one porous framework host configured to house a guest, and at least one guest being an oxidizer, where the guest is housed substantially within the host.

Embodiments of the invention include a host where the organic ligand(s) and the metal salts(s) form ligand/metal cluster(s) complex(es). In embodiments, the organic ligand(s) and the metal salts(s) form MOF host's designated $Zn_2NDC_2DPNI$, $Zn_2BDC_2BIPY$, IRMOF-9 and Basolite™ A100. The system may be in the form of an array of three dimensional porous framework(s). Embodiments of the system may further include a solvothermal combination mechanism. In embodiments, the solvothermal combination mechanism includes at least one of dimethylformamide (DMF), dimethylformamide (DEF), water, or other suitable solvent and a pre-determined amount of temperature applied to the complex depending on the ligand(s)/metal salt(s) complex utilized.

The ligand(s) include, but are not limited to, at least one of 2-6 napthalenedicarboxylic acid (NDC), N,N'-di(4pyridyl)-1,4,5,8-naphthalenetetracarboxydiimide (DPNI), 2-6 naphthalenedi-carboxylic acid (NDC), N,N'-di(4pyridyl)-1,4,5,8-naphthalenetetracarboxydiimide (DPNI), 1,4 benzene dicarboxylic acid (BDC), 1,3,5 benzene tricarboxylic acid (BTC), Biphenyl-4,4'-dicarboxylic acid (BPDC), 4,4' bypyridine (BIPY) and any combination thereof. The system may also include a porous framework(s) in the form of an amorphous powder(s), crystalline powder(s), and single crystal(s). In embodiments, the porous framework(s) is formed by at least one group of mechanisms involving change in temperature(s), pressure, solvent(s), gas(es), volatile curing agent(s), and any combination thereof.

Embodiments of the invention further include the removal of the host's preparative solvent before the addition of said oxidizer. Oxidizers in embodiments of the invention include; but are not limited to, at least one of ammonium perchlorate (AP), potassium perchlorate (KP), ammonium nitrate (AN), Ammonium dinitramide (ADN), Cyclotrimethylenetrinitramine (RDX), octogen (HMX), 2,4,6,8,10,12-hexanitro-2,4, 6,8,10,12-hexaazaisowurtzitane (CL-20), Guanadinium Dinitramide (Fox-12), dicyanodinitroethylene (Fox-7) or similar material and any combination thereof. Other embodiments of oxidizers include at least one of ammonium perchlorate (AP), ammonium nitrate (AN), and any combination thereof.

A variety of MOF hosts have been utilized in the this study (Examples include, $Zn_2(NDC)_2DPNI$, $Zn_4O(BPDC)_3$ (IRMOF-9) and Basolite™ A100 to occlude the common propellant oxidizers, ammonium perchlorate (AP) and ammonium nitrate (AN). It should be noted that although this study has only included AP and AN, any small molecule oxidizer of suitable size and solubility (examples Ammonium Dinitramide (ADN) Cyclotrimethylenetrinitramine (RDX), octogen (BMX), 2,4,6,8,10,12-hexanitro-2,4,6,8,10,12-hexaazaisowurtzitane (CL-20), Guanadinium Dinitramide (Fox-12), and dicyano-dinitro ethylene (Fox-7) could be introduced into the frameworks through this process. All of the MOFs utilized in this study are activated prior to the introduction of the oxidizer guest by heating the MOF to temperatures greater that 100° C. under reduced pressure over an 8 hr period. Once activated, the MOF is then subjected immediately to the oxidizer guest inclusion procedure or stored in a desiccator. Ammonium perchlorate and Ammonium Nitrate were chosen as the solid oxidizer materials for this study based upon their widespread use in missile systems currently fielded by the US armed forces.

Bulk Preparation of MOF-Oxidizer Complexes

To the dry powder of activated MOF was added a saturated solution of oxidizer (the AP was saturated in DMF while the AN is in an aqueous solution) The MOF crystals were allowed to soak in the saturated oxidizer solution for a period of 30 days. Every 7 days, the soaking solution was replaced with fresh saturated oxidizer solution. The crystals with collected by vacuum filtrations and washed with either DMF or water depending on the nature of oxidizer solution. The MOF-Oxidizer complexes were characterized by differential scanning calorimetry (DSC) and thermal gravimetric analysis (TGA)

DSC and TGA of the MOF-Oxidizer Host/Guest Complex.

Figure 9A:
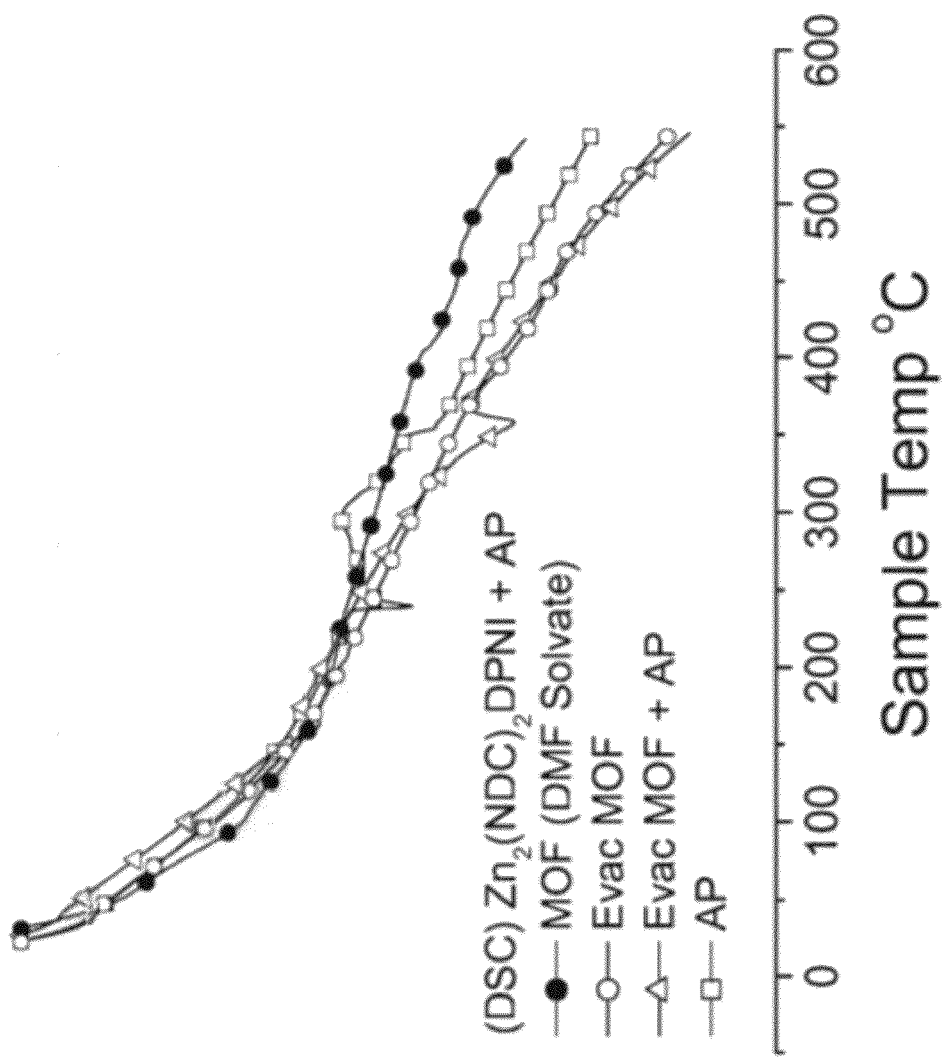
FIG. 9A is a graph illustrating DSC data for the $Zn_2(NDC)_2$DPNI-DMF and $Zn_2(NDC)_2$DPNI-AP complexes as well as neat Ammonium Perchlorate, according to embodiment of the invention.
Figure 9B:
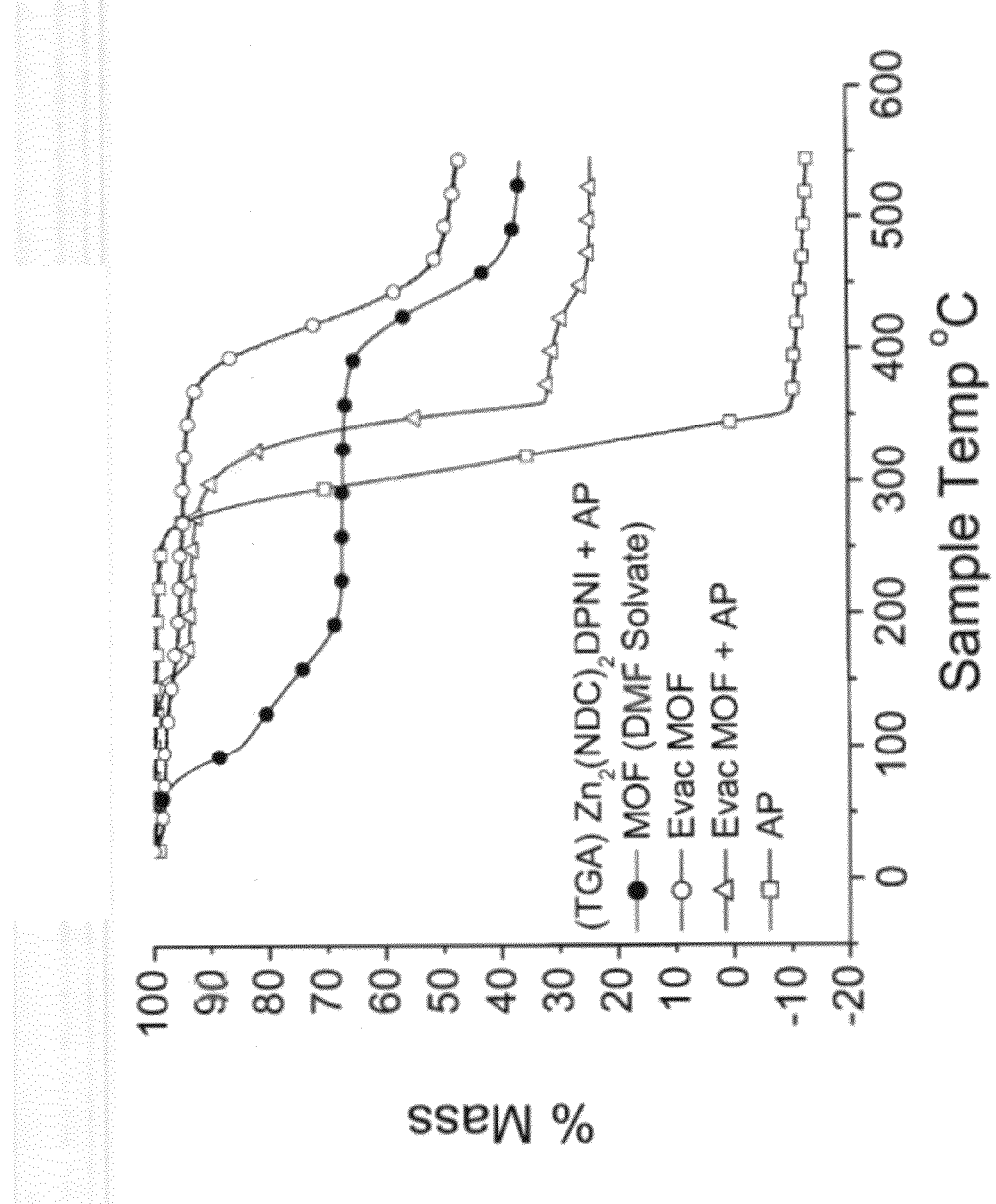
FIG. 9B is a graph illustrating TGA data for the $Zn_2(NDC)_2$DPNI-DMF and $Zn_2(NDC)_2$DPNI-AP complexes as well as neat Ammonium Perchlorate, according to embodiment of the invention.

$Zn_2(NDC)_2DPNI$-Ammonium Perchlorate Complex:

The DSC and TGA traces of the $Zn_2(NDC)_2DPNI$-Ammonium Perchlorate Complex overlaid with comparison traces of the initial MOF as well as the unoccluded guest are illustrated in FIGS. 9A and 9B. From the data, the MOF-AP complex shows an initial endotherm at 164° C. which can be assigned to the loss of occluded DMF present as a result of utilizing a saturate DMF solution to introduce the oxidizer guest. This initial endotherm is followed by a larger endotherm at 357° C. which has been assigned as the decomposition of the AP guest. This is followed by framework decomposition around 425° C. The TGA data corroborates the DSC data with three distinct weight loss events corresponding to loss of DMF followed by AP and finally framework decomposition. By comparison to the DSC traces for neat AP, an increase in the peak decomposition temperature of 57° C. was observed for the MOF occluded AP.

Figure 10A:
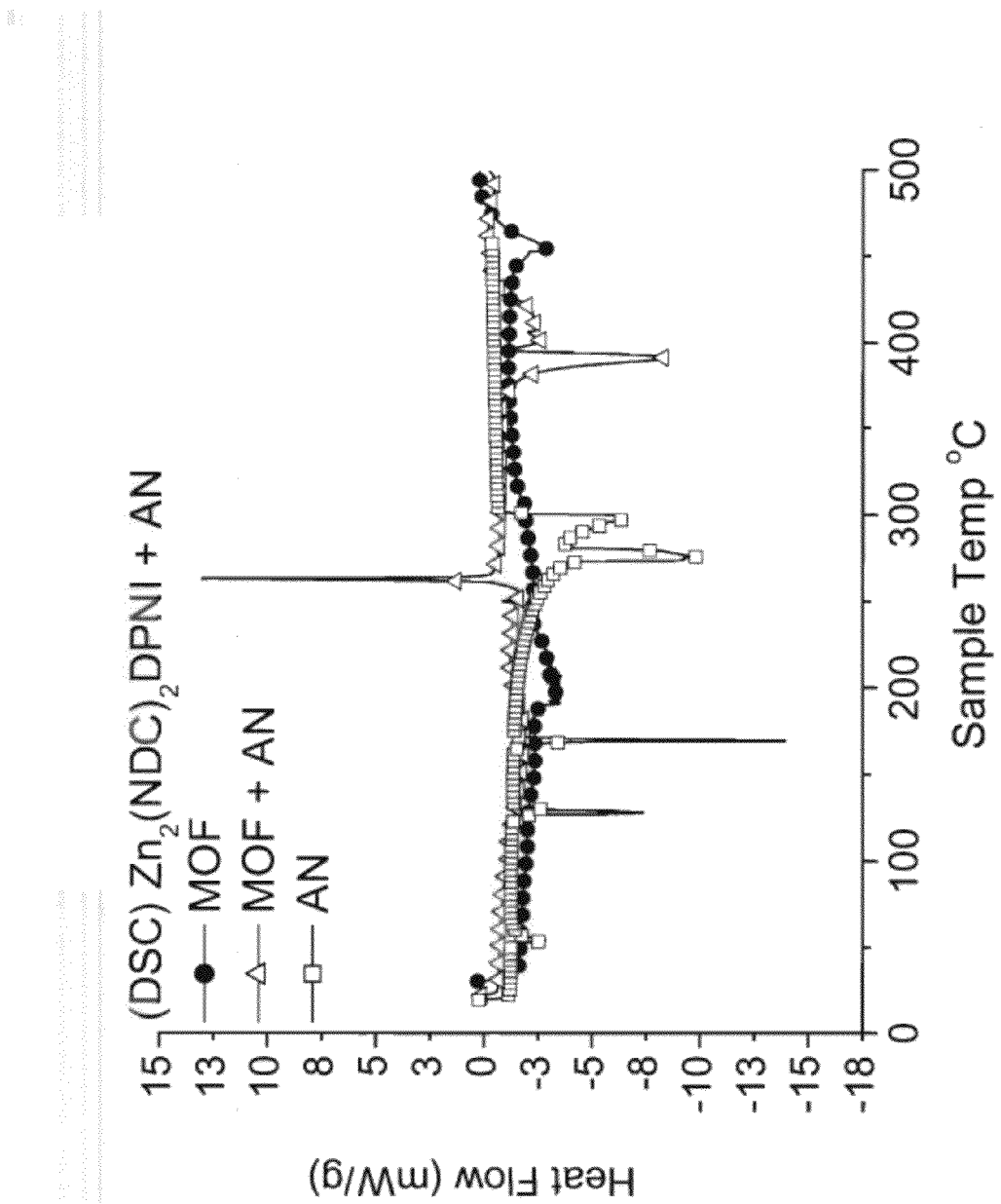
FIG. 10A is a graph illustrating DSC data for the $Zn_2(NDC)_2$DPNI-DMF and $Zn_2(NDC)_2$DPNI-AN complexes as well as neat Ammonium Nitrate, according to embodiment of the invention.
Figure 10B:
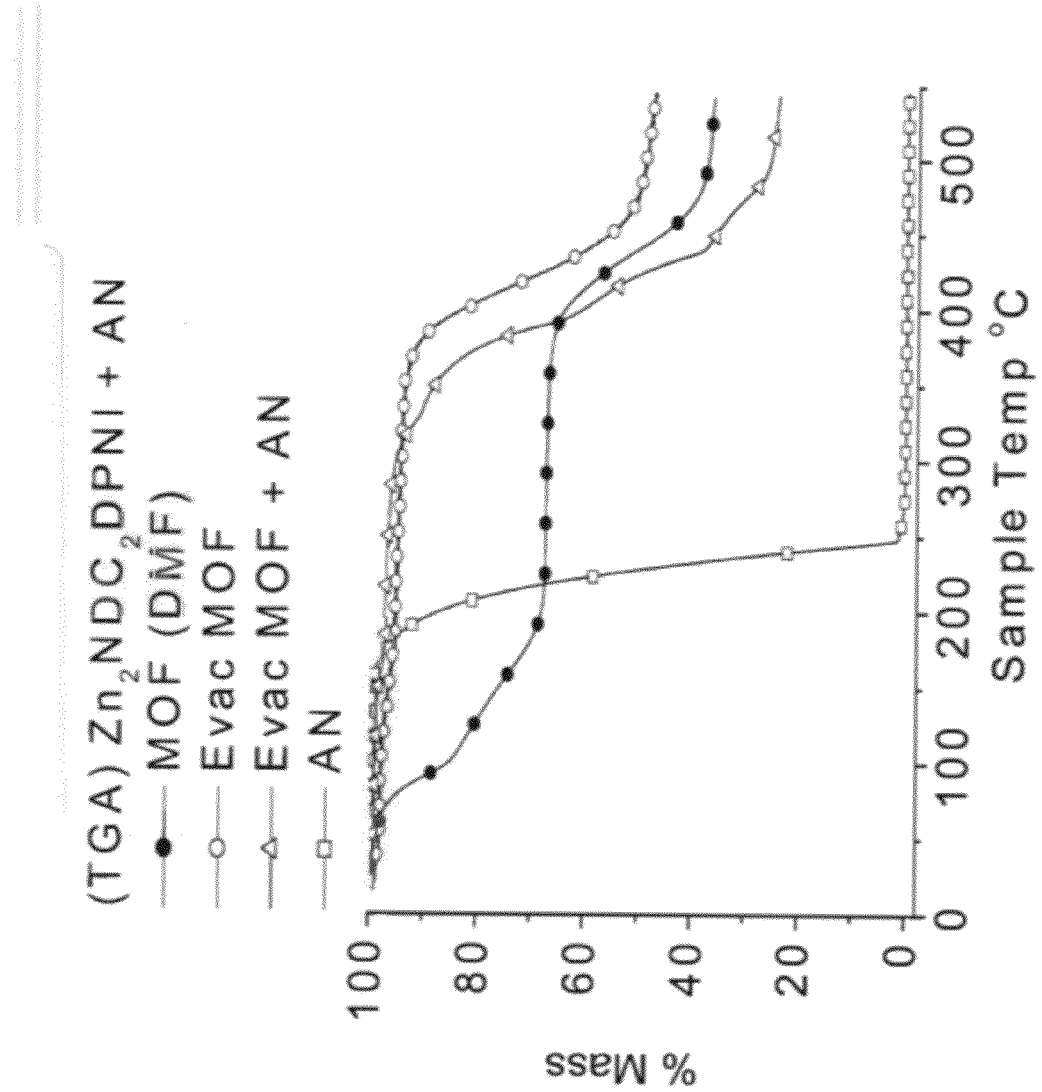
FIG. 10B is a graph illustrating TGA data for the $Zn_2(NDC)_2$DPNI-DMF and $Zn_2(NDC)_2$DPNI-AN complexes as well as neat Ammonium Nitrate, according to embodiment of the invention.

$Zn_2(NDC)_2DPNI$ -Ammonium Nitrate Complex:

The DSC and TGA traces of the $Zn_2(NDC)_2DPNI$ -Ammonium Nitrate Complex overlaid with comparison traces of the initial MOF as well as the unoccluded guest are illustrated in FIGS. 10A and 10B. Observed from the DSC traces for the MOF-AN complex a strong exothermic peak at 263° C. which corresponds directly to neat ammonium nitrate. It can therefore be assigned as AN coated on the surface of the MOF crystals which survived the washing procedure. This exothermic peak is followed by a strong endothermic decomposition peak at 391° C. which is quickly followed by another weaker endotherm at 401° C. By comparison to the TGA data the first of these endothermic decomposition peaks can be assigned to the decomposition of the occluded AN followed by the framework decomposition at 401° C. By comparison to the DSC traces of neat AN we see an increase in the peak decomposition temperature of 116° C. as a result of AN occlusion.

It is also important to note that the occluded AN exhibits none of the lower temperature phase changes (endothermic peaks at 54, 128, & 169° C.) exhibited by the neat oxidizer. The phase stabilization of AN in addition to the increase in thermal stability is an important consequence of MOF-AN host guest encapsulation since the low-temperature phase changes associated with bulk AN limit its use in long shelf life high energy rocket propellants.

Figure 11A:
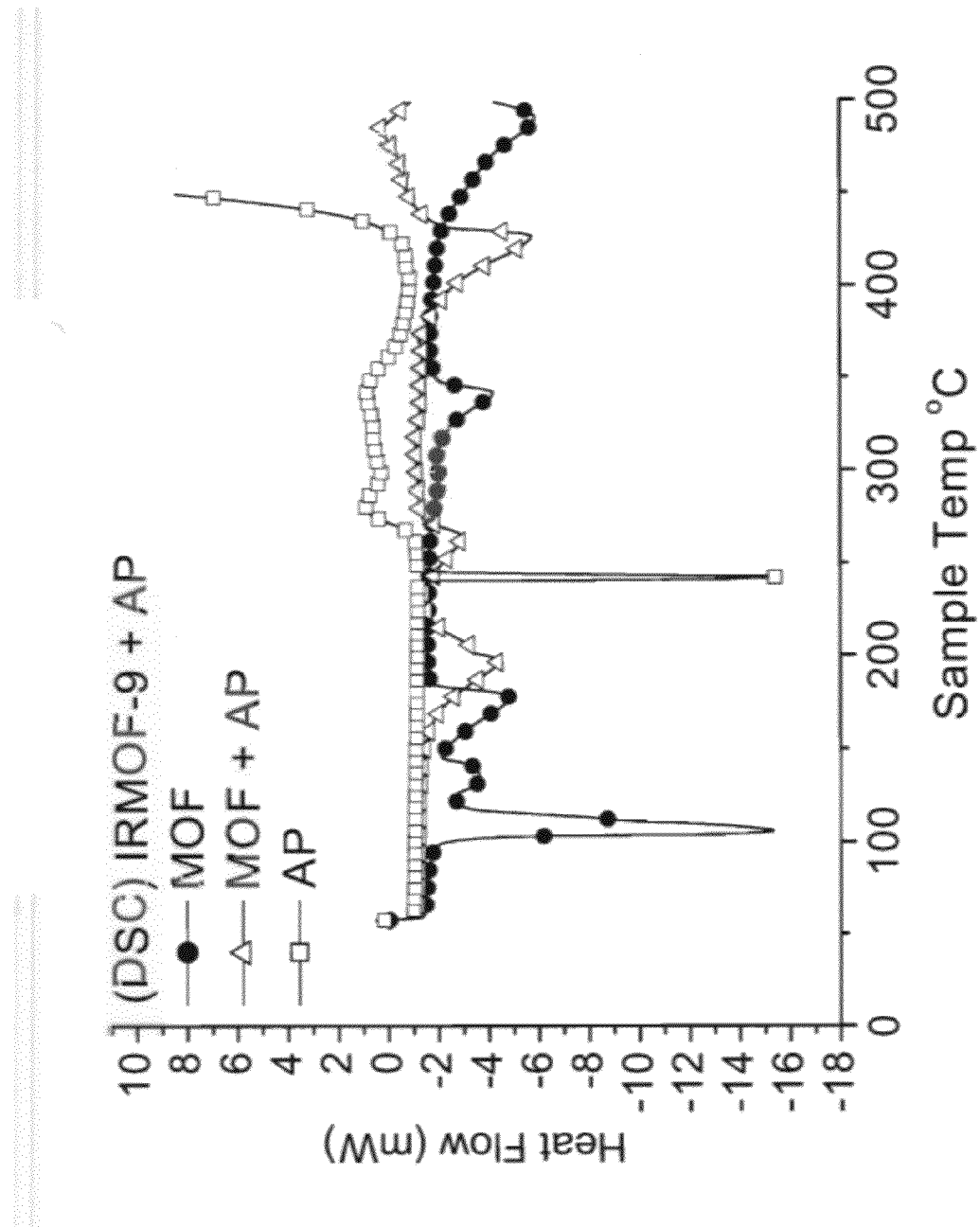
FIG. 11A is graph illustrating DSC data for the IRMOF-9-DMF and IRMOF-9-AP complexes as well as neat Ammonium Perchlorate, according to embodiment of the invention.
Figure 11B:
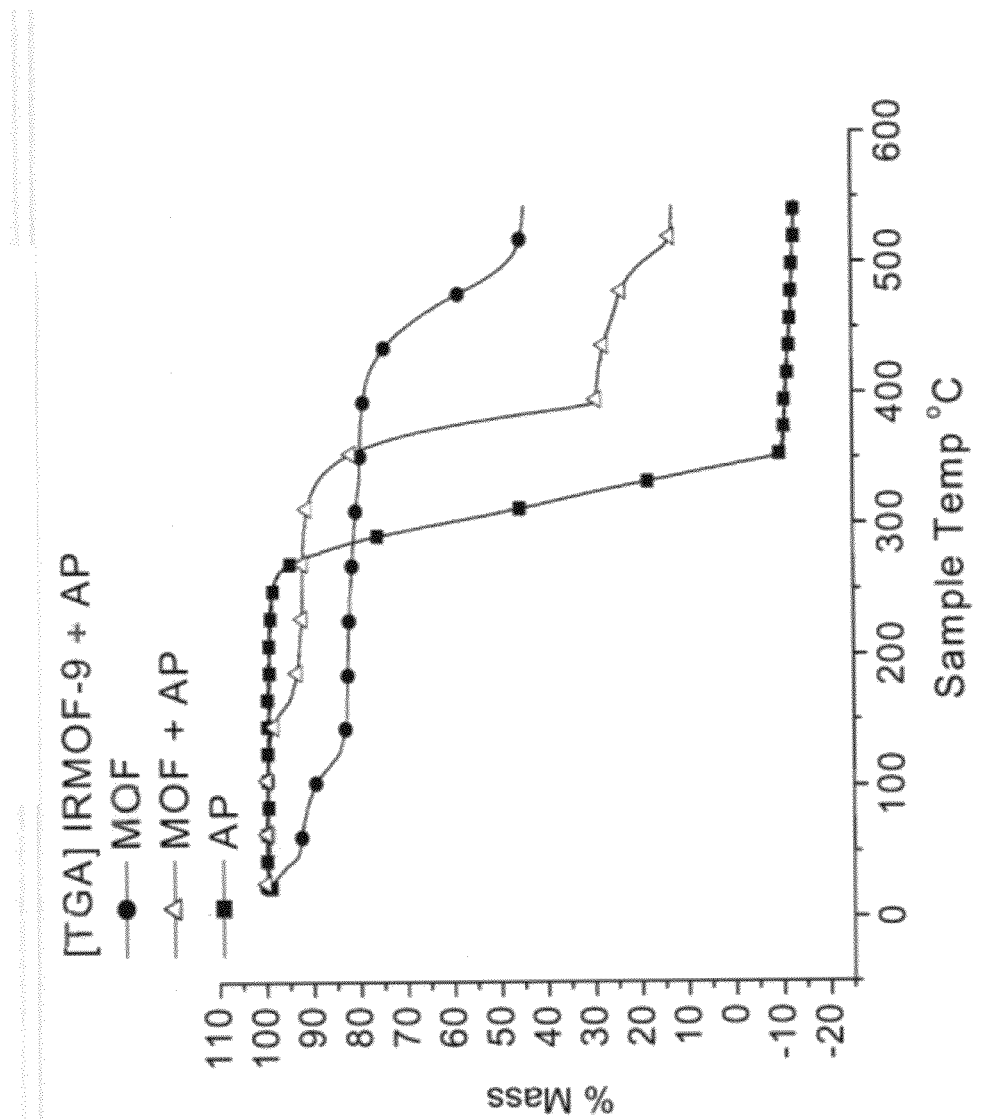
FIG. 11B is a graph illustrating TGA data for the IRMOF-9-DMF and IRMOF-9-AP complexes as well as neat Ammonium Perchlorate, according to embodiment of the invention.

$Zn_4O(BDC)_3$-Ammonium Perchlorate Complex (IRMOF-9-AP):

FIGS. 11A and 11B illustrates the DSC and TGA traces for the IRMOF-9 complex with AP. The DSC trace for the MOF-AP complex shows four distinct events which can be assigned by comparison to the TGA data. The first two endothermic signals at 197° C. and 264° C. can be assigned as the lost of surface bound and occluded DMF still present following oxidizer inclusion and the phase change of the occluded AP respectively. These are followed by a strong endothermic decomposition peak at 426° C. which can be assigned to the decomposition of the entrapped AP. This decomposition is followed by exothermic decomposition of the framework at 485° C. By comparison to the DSC traces of neat AP (peak decomposition at 281° C.), an increase in the peak decomposition temperature of 145° C. going from the neat AP to the MOF occluded AP was observed.

Figure 12A:
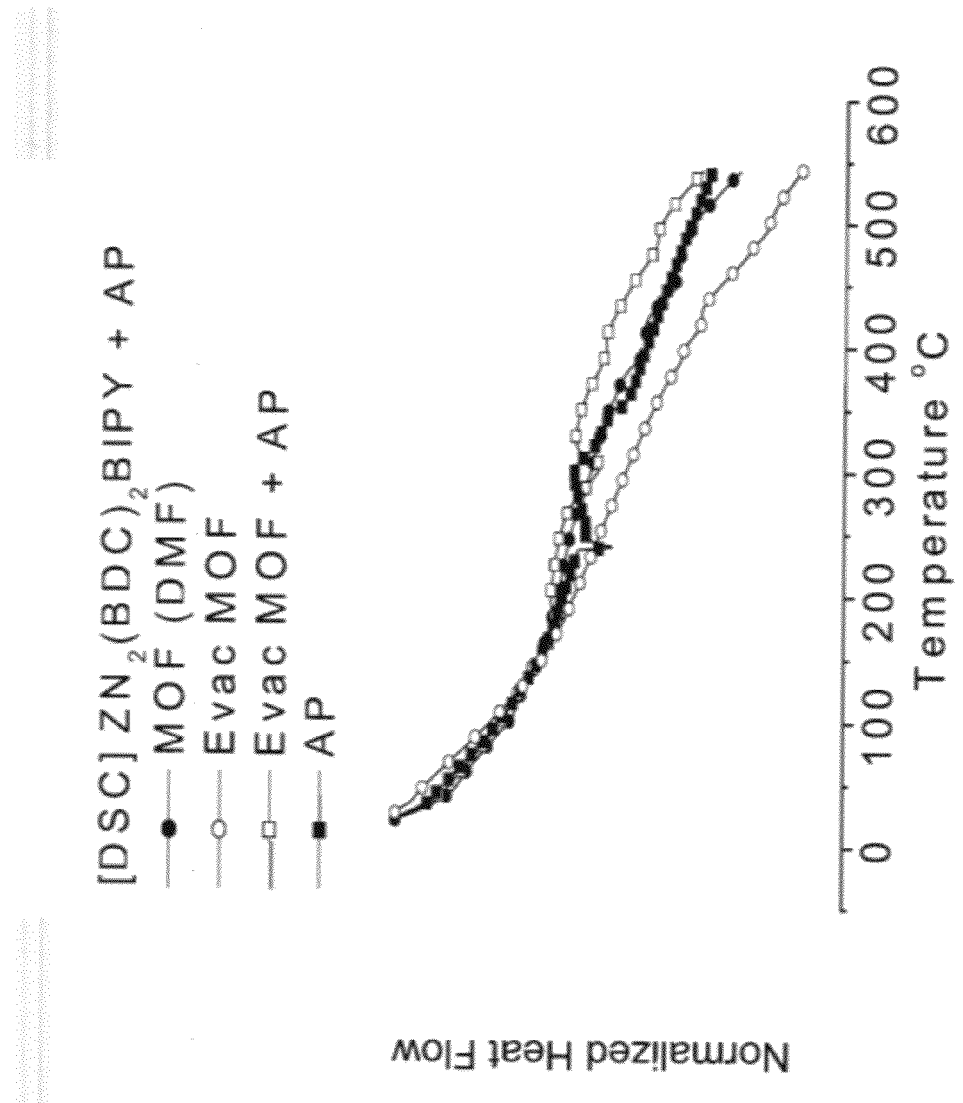
FIG. 12A is a graph illustrating DSC data for the $Zn_2(BDC)_2$BIPY-DMF and $Zn_2(BDC)_2$BIPY-AP complexes as well as neat Ammonium Perchlorate, according to embodiment of the invention.
Figure 12B:
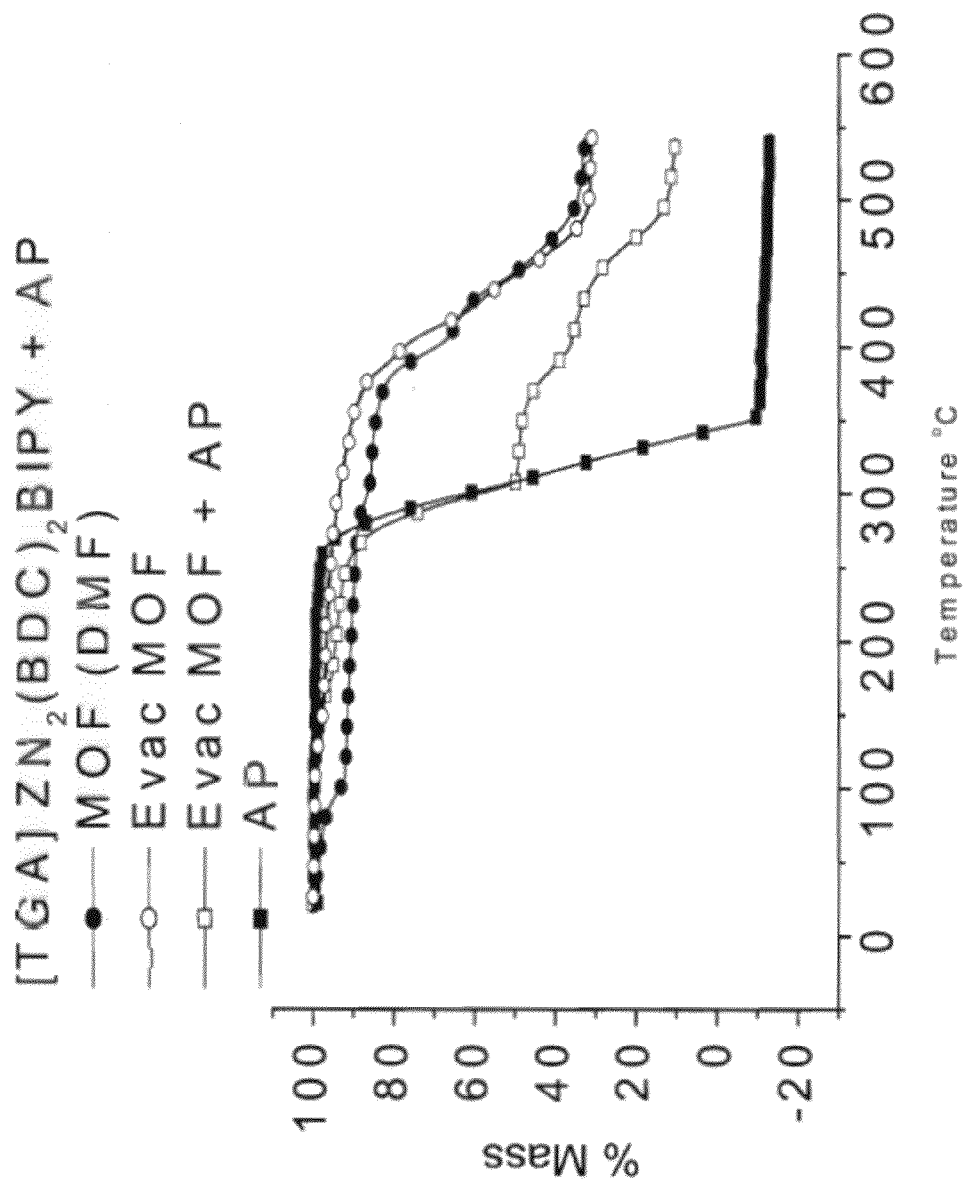
FIG. 12B is a graph illustrating TGA data for the $Zn_2(BDC)_2$BIPY-DMF and $Zn_2(BDC)_2$BIPY-AP complexes as well as neat Ammonium Perchlorate, according to embodiment of the invention.

$Zn_2(BDC)_2BIPY$-Ammonium Perchlorate Complex:

FIGS. 12A and 12B illustrates the DSC and TGA trances for the $Zn_2(BDC)_2BIPY$ complex with AP. The DSC trace for the MOF-AP complex shows three distinct events which can be assigned by comparison to the TGA data. The first of the endothermic signals at 186° C. can be assigned as the lost of occluded DMF still present following oxidizer inclusion. The next endothermic signal at 315° C. can be assigned to the decomposition of the AP. It is an important distinction that the $Zn_2(BDC)_2BIPY$ appears to have little to no effect on the thermal decomposition of the AP. The is corroborated by the TGA data which shows not change in the temperature of weight loss between the neat AP and the AP added to the MOF. This is likely due to the relative size of accessible pores in the $Zn_2(BDC)_2BIPY$ MOF. It appears as though the AP is unable to penetrate into the core of the framework and remains solely on the surface of the crystals. The failure of the $Zn_2(BDC)_2BIPY$ MOF to effect the thermal behavior of the intended guest further accentuates the benefit of oxidizer encapsulation demonstrated by the MOFs with accessible pores In these tests we see that as a consequence of successful encapsulation of the oxidizer guest within the pores of the MOF framework we observe increases in the thermal decomposition temperature of greater than 50° C. with some effects as large as 145° C. In addition to thermal stability the encapsulation of Ammonium Nitrate within the MOF pores appears to phase stabilize the guest. This is an import feature for increasing the viability of AN for use in long shelf life high performance rocket motors These tests confirm the hypothesis that encapsulation of a solid oxidizer within the pores of a thermally stable host brings about significant enhancement in the thermal stability of the guest.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A host-guest complex as an energetic component in an insensitive munitions weapons system, comprising:
   an effective amount of at least one host having organic ligand(s) combined with an effective amount of at least one metal salt to form ligand(s)/metal salt(s) complex, wherein said ligand(s)/salt(s) complex form at least one porous framework host configured to house a guest, wherein said host is Aluminum terephthalate; and
   at least one said guest being a liquid energetic/explosive material, wherein said guest is housed substantially within said host.

2. The system according to claim 1, wherein said organic ligand(s) and said metal salts(s) form ligand/metal cluster(s) complex(es).

3. The system according to claim 1, wherein said system being in the form of an array of three dimensional porous framework(s).

4. The system according to claim 1, wherein said ligand(s) comprises at least one of 2-6 naphthalenedicarboxylic acid (NDC), N,N'-di(4pyridyl)-1,4,5,8-naphthalenetetracarboxydiimide (DPNI), 1,4 benzene dicarboxylic acid (BDC), and any combination thereof.

5. The system according to claim 1, further comprising a solvothermal combination mechanism.

6. The system according to claim 5, wherein said solvothermal combination mechanism comprising at least one of dimethylformamide (DMF) solvent and a pre-determined amount of temperature applied to said complex depending on said ligand(s)/metal salt(s) complex utilized.

7. The system according to claim 5, further comprising replacement of solvent with said liquid energetic/explosive material.

8. The system according to claim 1, wherein said liquid energetic/explosive material comprises at least one of n-butyl-2-nitratoethylnitramine (BuNENA), butanetriol trinitrate (BTTN), tetramethylolethane trinitrate (TMETN), triethylenegylcol dinitrate (TEGDN), nitroglycerine (NG), diethyleneglycol dinitrate (DEGDN), and other similar material, and any combination thereof.

9. The system according to claim 1, wherein said porous framework(s) is in the form of an amorphous powder(s), crystalline powder(s), and single crystal(s).

10. The system according to claim 1, wherein said porous framework(s) is formed by at least one group of mechanisms involving change in temperature(s), pressure, solvent(s), gas(es), volatile curing agent(s), and any combination thereof.

* * * * *